US005364386A

United States Patent [19]

[11] Patent Number: 5,364,386

Fukuoka et al.

[45] Date of Patent: Nov. 15, 1994

[54] INFUSION UNIT

[75] Inventors: Hisaji Fukuoka, Soka; Tatsuji Yoshida, Washinomiya; Suminori Kobayashi, Yachiyo; Toshikazu Sakurai, Noda, all of Japan

[73] Assignee: Hikari Seiyaku Kabushiki Kaisha, Tokyo, Japan

[21] Appl. No.: 58,544

[22] Filed: May 5, 1993

[51] Int. Cl.[5] .............................................. A61B 19/00

[52] U.S. Cl. .................................... 604/411; 604/414; 604/415; 604/82; 604/86; 604/87; 604/88; 604/89; 604/91; 604/56; 222/83; 215/247; 215/DIG. 8; 215/DIG. 3

[58] Field of Search .............................. 604/56, 82–92, 604/411–415; 222/81, 83, 83.5, 88, 129; 215/247, DIG. 8, DIG. 3; 206/219, 222

[56] References Cited

U.S. PATENT DOCUMENTS 3,995,630 12/1976 van de Veerdonk .
4,411,662 10/1983 Pearson .
4,467,588 8/1984 Carveth .
4,581,016 4/1986 Gettig .
4,583,971 4/1986 Bocquet et al. .
4,871,354 10/1989 Conn et al. .......................... 604/89
4,936,841 6/1990 Aoki et al. .......................... 604/413
5,080,649 1/1992 Vetter .
5,152,965 10/1992 Fisk et al. .
5,186,323 2/1993 Pfleger .................................. 222/83

*Primary Examiner*—David Isabella
*Assistant Examiner*—P. Zuttarelli
*Attorney, Agent, or Firm*—Christie, Parker & Hale

[57] ABSTRACT

An infusion unit has a flexible container and an open-ended pipe having a first opening in communication with the container and a second opening axially opposite the first. The pipe has smaller and larger diameter portions with the smaller diameter portion located between the second opening and the larger diameter portion. An axially moveable plug is receivable within the smaller diameter portion to seal the second opening of the pipe. An axially moveable engaging member with an end for engaging the plug and a needle at the opposite end for piercing the stopper of a vial. The plug may be pushed by the engaging member from the smaller diameter section to the larger diameter section so as to permit flow through the pipe between the first and second openings to the vial and container.

11 Claims, 5 Drawing Sheets

INFUSION UNIT

BACKGROUND OF THE INVENTION

This invention relates to an infusion unit for use in medical services and, in particular, to a kit capable of dissolving a powder medicine into a solvent liquid or a diluent liquid immediately before use, with a very simple operation.

In medical institutions, various medical kits combining medicines and medical instruments are widely used in order to reduce work load in preparation of doses and to prevent bacterial contamination and entry of foreign matter.

Generally, an infusion fluid for drip injection is prepared before every use by removing powdery medicine from a vial and dissolving it into a diluent liquid such as a sugar solution or a saline solution. Because of frequent use of such infusion solution, there has been a longstanding demand to simplify preparation.

A conventional infusion unit or kit generally comprises a holder for holding a medicine bottle or vial with a mouth at one end thereof sealed by a pierceable mouth-plug, a flexible liquid container and communicating means for communication between the medicine bottle and the flexible liquid container. The communicating means comprises a piercing needle provided on the vial and a tear member provided on the flexible liquid container. After the mouth-plug which is typically made of rubber, has been pierced with the piercing needle, the tear member is manually torn off so that the medicine bottle and the flexible liquid container communicate with each other (Japanese National Laid-Open Publication No. Sho 61-501129). The communicating means may also comprise a double-pointed needle, so that both the medicine bottle and the liquid container are pierced with the doublepointed needle for communication therebetween to allow the contents to mix (Japanese Patent Laid-Open Publication No. Hei 2-1277).

However, the above-mentioned first conventional infusion unit with the tear member requires a troublesome tearing operation. If the tearing operation provides an insufficient opening, dissolution takes a long time because only a small quantity of medicine is able to flow through the opening. In addition, scraps of the tear member may be dropped into the infusion solution. The above-mentioned second conventional infusion unit with the double-pointed needle requires control means of a special design for controlling communication in such a manner that one end of the double-pointed needle first pierces through the mouth-plug of the medicine bottle before the other end pierces through a sealing film of the flexible liquid container. Since the operation of the control means cannot be known intuitively, an operator may get confused in case of emergency.

The present invention provides an infusion unit which is capable of assuring a tight seal of a liquid container before use and which is capable of establishing reliable communication between a medicine bottle while avoiding the problems of the prior art.

SUMMARY OF THE INVENTION

According to the invention an infusion unit is provided that has a flexible container and an open-ended pipe having a first opening in communication with the container and a second opening axially opposite the first. The pipe also has smaller and larger internal diameter portions with the smaller diameter portion located between the second opening and the larger diameter portion. An axially moveable plug is receivable within the smaller diameter portion to seal the second opening of the pipe. An axially moveable engaging member is included that has an end for engaging the plug and a needle at the opposite end for piercing the stopper of a vial. The plug may be pushed by the engaging member from the smaller diameter section to the larger diameter section so as to permit flow between the first and second openings through the pipe and between the vial and the container.

BRIEF DESCRIPTION OF THE DRAWINGS

The foregoing and other features and advantages of the present invention will be appreciated as the same becomes understood by reference to the following detailed description, when considered in connection with the accompanying drawings wherein.

DETAILED DESCRIPTION

Figure 1:
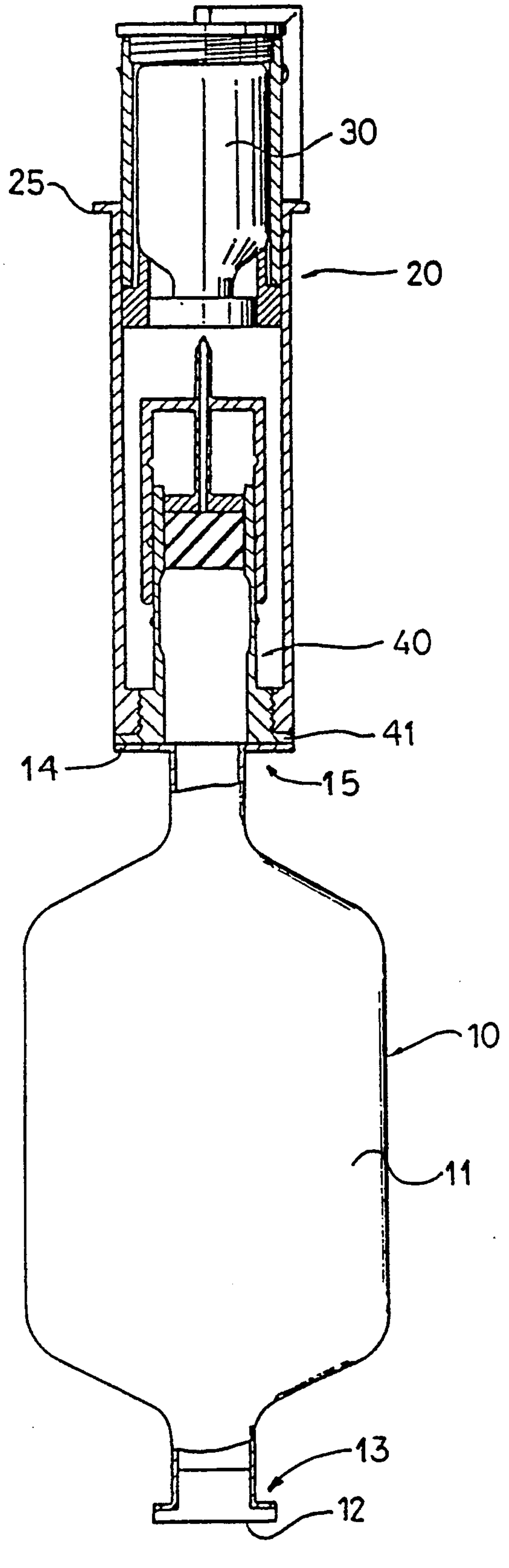
FIG. 1 is a cross-sectional view of an infusion unit according to one embodiment of the present invention.

A flexible liquid container 10 is provided to hold a solvent liquid or a diluent liquid (hereinafter referred to as a solvent liquid). A holder 20 holds a medicine bottle or vial 30 and a coupling portion 40 couples the flexible liquid container 10 and the holder 20.

The liquid container 10 comprises a flexible transparent bag 11 formed of soft resin such as polyvinyl chloride, polyolefin or ethylene-vinyl acetate copolymer. The liquid container 10 has an outlet 12 at its lower end 13 to discharge a solution for infusion after medicine has been dissolved. The liquid container 10 has an annular flange 14 at its upper end 15 which is fusion-bonded to an annular flange 41 at the lower end or base **40*a* of the coupling portion 40 to establish communication between the interior of the liquid container and the interior of a communicating pipe 42 formed unitarily with, and extending upward from, the annular flange 40 and base 40*a* (FIG. 2**).

Figure 2:
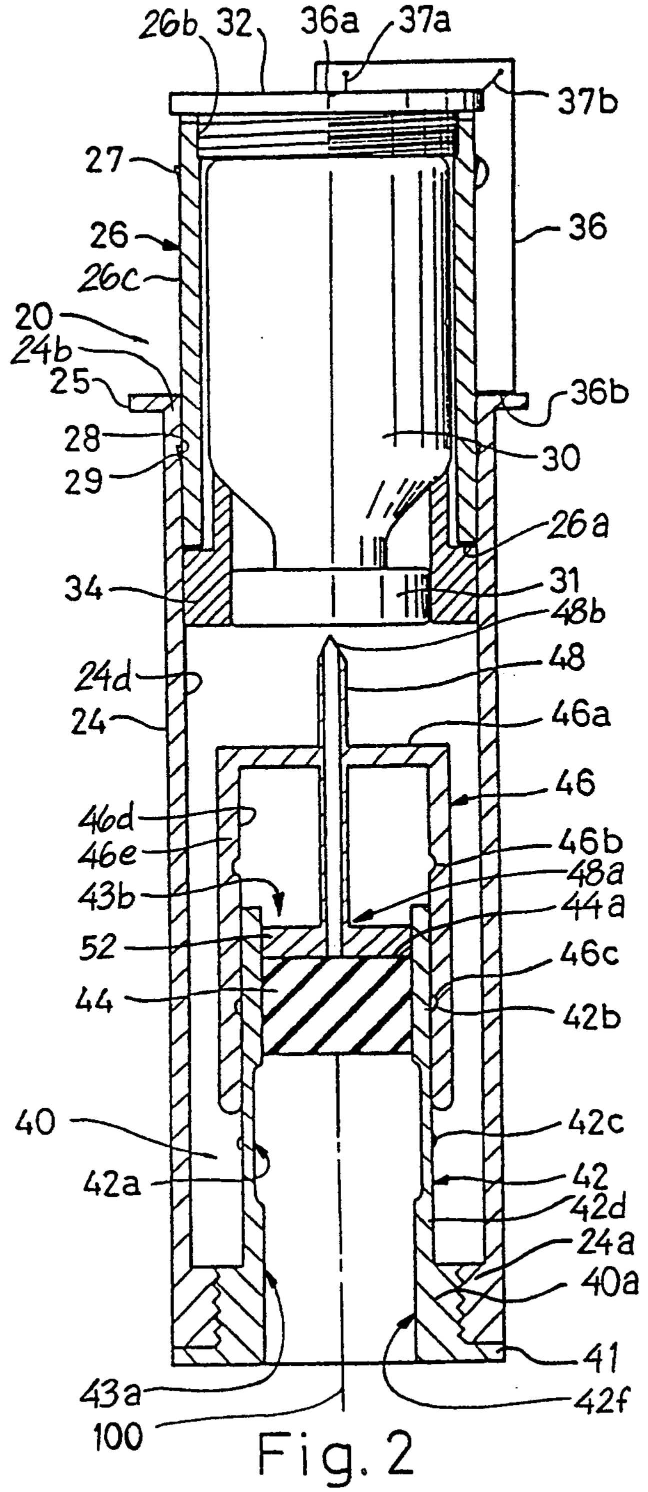
FIG. 2 is a cross-sectional view of a holder and a coupling portion of the infusion unit of FIG. 1, in a pre-use disengaged configuration.
Figure 3:
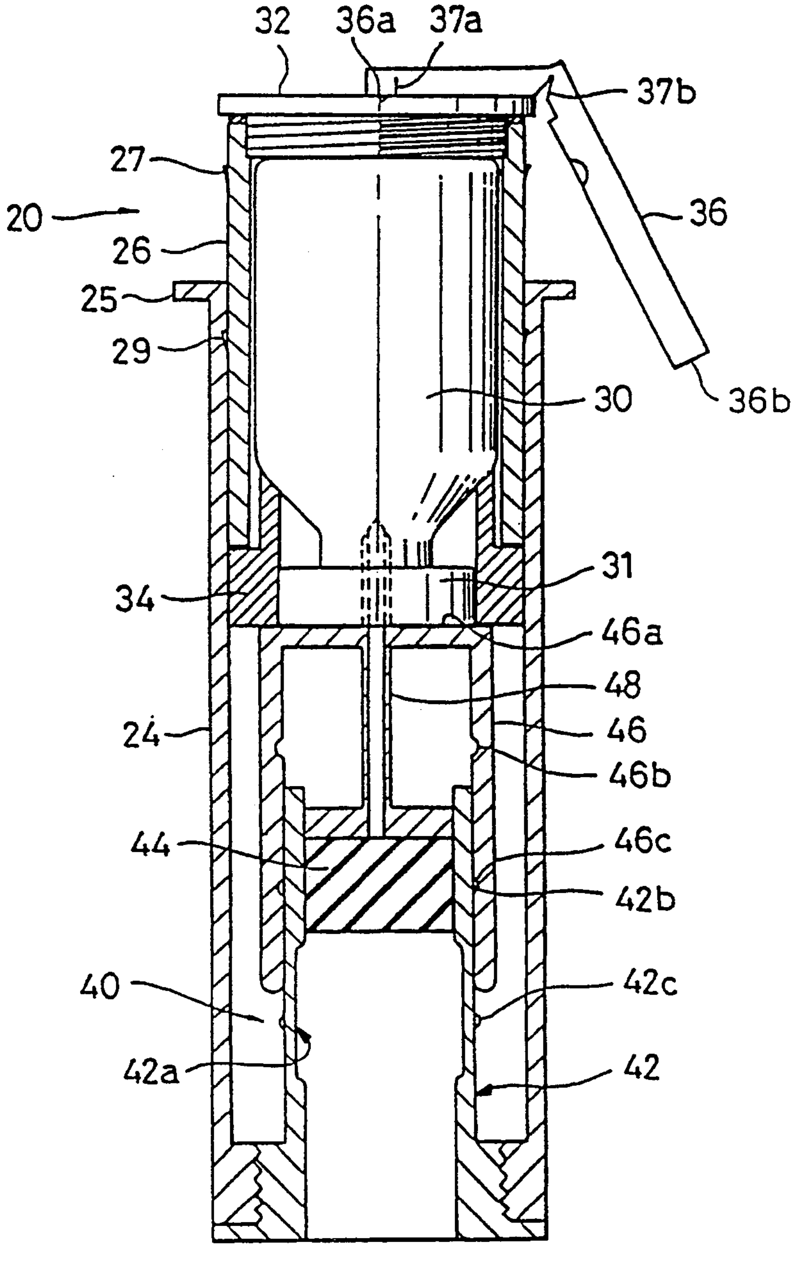
FIG. 3 is a cross-sectional view of the holder and coupling portion of the infusion unit of FIG. 1, in a partially engaged configuration.
Figure 4:
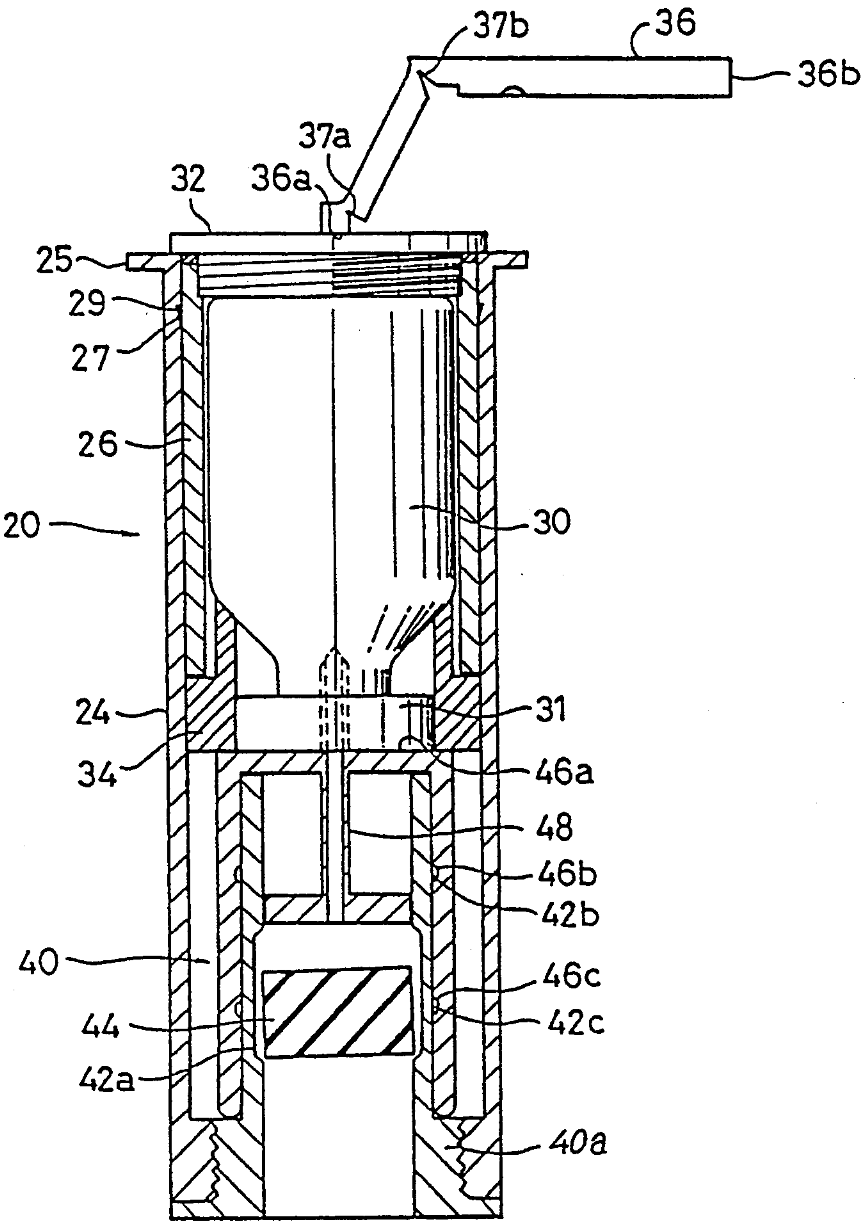
FIG. 4 is a cross-sectional view of the holder and coupling portion of the infusion unit of FIG. 1 in a fully engaged configuration.

The holder 20 comprises an outer cylindrical sleeve 24 and an inner cylindrical sleeve 26 both coaxial about an axis 100 of the communicating pipe 42 (FIG. 2). The outer sleeve 24 has an internally threaded lower end **24*a* screwed onto the base 40*a* of the coupling portion which is externally threaded. The inner sleeve 26 is slidably fitted into the upper end 24*a* of the outer sleeve. An annular flange 25 is formed at the upper end of the outer sleeve and serves as a hand grip for an operator's fingers (not shown) when the inner sleeve is inserted into the outer sleeve. The inner sleeve 26 is provided with upper and lower ribs, 27 and 28 respectively, on its outer peripheral surface 26*c***. The inner sleeve is axially moveable relative to the outer sleeve and can be fixed at two different positions by fitting either one of the ribs 27 or 28 into a peripheral groove 25 formed on the inner surface 24d of the outer sleeve 24. The inner sleeve 26 has an internally threaded upper end 26b sealed by a screw cap 32. With the screw cap removed, the vial 30 is inserted into the inner sleeve through its upper end. A rubber ring 34 for supporting the vial 30 is provided at the lower end 26a of the inner sleeve and kept in slidable contact with the inner surface of the outer sleeve. The rubber ring 34 supports the vial, keeps an airtight seal with the vial, and prevents chattering of the inner sleeve when moved. A hanger 36 has an upper end 36a fixedly attached to the screw cap and a lower end 36b. When the infusion unit is not in use, the lower end 36b is brought into contact with the flange 25 of the outer sleeve by pressure to prevent the movement of the inner sleeve. In use, the hanger 36 is flexed so that hanger portions 37a and 37b are expanded as shown in FIGS. 3 and 4, and the infusion unit is hung in an appropriate position such as by a hook (not shown) formed at the lower end 36b.

The coupling portion has a lower opening 43a bounded by the base 40a and in communication with the container. The coupling portion further includes a plug member or a rubber plug 44 which is located in an upper portion 42e of the communicating pipe 42 adjacent to upper opening 43b and an axially movable cap member 46 placed over the communicating pipe 42 at the upper opening 43b adjacent the medicine bottle. The communicating pipe 42 has an enlarged portion 42a formed axially intermediate its upper and lower openings having a larger inner diameter than the upper section 42e or a lower section 42f adjacent the lower opening 43a. The rubber plug 44 is located in the upper portion 42e above the enlarged portion 42 to seal the communicating pipe 42 adjacent the upper opening by friction. The movable cap member 46 also covers the upper opening of the communicating pipe. The movable cap member 46 has a unitary piercing needle 48 located partially within the communicating pipe 42. The piercing needle 48 extends axially upward through the top 46a of the movable cap member 46 toward the mouth-plug 31 of the vial 30. An annular flange 52 having a diameter substantially equal to that of the rubber plug 44 is formed at the lower end 48a of the piercing needle 48 and located within the communicating pipe 42. The flange 48a is in contact with the top surface 44a of the rubber plug. The communicating pipe 42 is provided on its outer peripheral surface 42d with upper and lower ribs 42b and 42c selectively engageable with peripheral grooves 46b and 46c formed on the inner surface 46d of the annular collar portion 46e of the movable cap member 46. Thus, the movable cap member 46 can be fixed at either of two different positions.

Operations of the infusion unit in use are described below with reference to FIGS. 2, 3 and 4.

Initially, the movable cap member 46 is positioned at a first position corresponding to a pre-use, disengaged configuration with the rubber plug 44 located above the enlarged portion 42a of the communicating pipe 42 to seal the communicating pipe 42 adjacent its upper opening 43b (FIG. 2). In this state, the flange at the lower end of the piercing needle is in contact with the top 44a of the rubber plug and, the movable cap member 46 is prevented from moving toward the liquid container by both friction between the rubber plug and the pipe and interaction of rib 42b with groove 46c.

After the hanger 36 has been disengaged from the outer sleeve 24, the screw cap 32 is inwardly inserted by an operator while the operator holds the flange 25 of the outer sleeve 24, so as to move the inner sleeve 26 and vial 30 axially toward the needle. The mouth-plug 31 of the vial 30 has a center portion (not shown) formed of a rubber film enabling tip blade 48b of the piercing needle to pierce through the mouth-plug as shown in FIG. 3. In this state, the mouth-plug is brought into contact with the top of the movable cap member to achieve an intermediate (partially engaged) configuration. When the vial is further inserted, the operating force directly acts on the rubber plug 44 through the flange 52 at the lower end of the piercing needle to overcome a frictional force between the rubber plug and the communicating pipe and the interaction of the rib 42b with the groove 46c. As a result, the rubber plug is pushed toward and dropped into the enlarged portion of the communicating pipe.

When the movable cap member reaches a second (fully engaged configuration) position, the rubber plug is now free inside the enlarged portion so that a gap is produced around the rubber plug (FIG. 4). At this stage, the interiors of the vial and the liquid container have finally come into communication with each other permitting the respective contents to mix.

In this configuration, the flexible liquid container is pressed or squeezed to deliver the solvent liquid in the liquid container to the vial and to return the solvent liquid back from the vial. Thus, the powdery medicine contained in the vial is dissolved, and the resulting solution may be discharged as an infusion solution through a tube (not shown) connected to the outlet of the liquid container.

Figure 5:
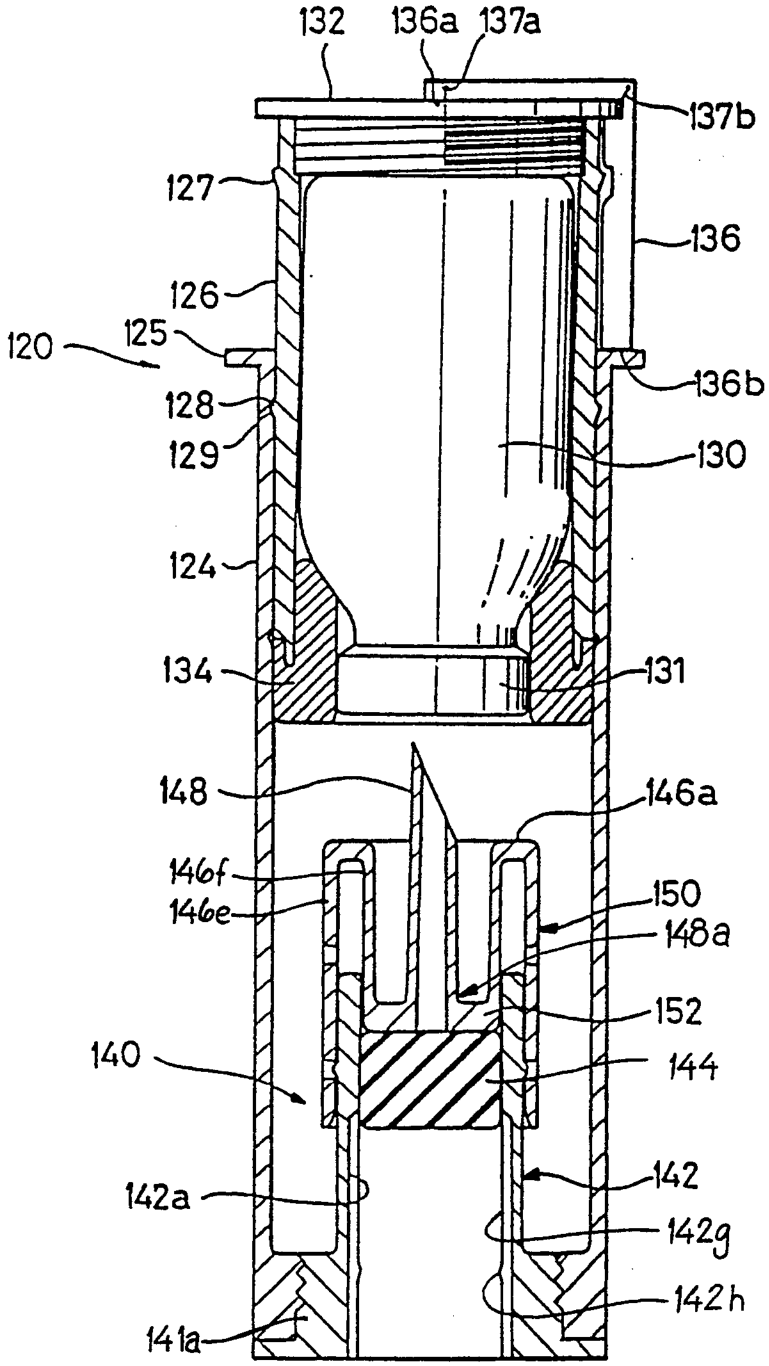
FIG. 5 is a cross-sectional view of a holder and a coupling portion of a second infusion unit according to principles of the invention.

FIG. 5 is a sectional view of another embodiment of a holder and coupling portion of an infusion unit according to this invention. This embodiment is substantially similar to the preceding embodiment except that a movable cap member 150 and communicating pipe 142 have different shapes. Similar parts are designated by the same reference numerals plus one hundred as in previous figures and thus operations are the same.

According to this embodiment, the movable cap member 150 has a structure such that the lower end 148a of the piercing needle 148 is formed into a flange 152 having a peripheral portion which is connected to the annular top 146a through an inner collar portion 146f extending along the inner surface of the communicating pipe. The movable plastic cap member of this embodiment can be made by a molding process. In addition, it is possible to completely prevent leakage of solution from the communicating pipe after the rubber plug has been dropped, because the annular top seals against the rubber ring 134 as the mouth-plug 131 is recessed relative to the ring.

The enlarged portion 142a extends all the way through the base 140a. The portion is provided with axial ribs 142g which maintain the orientation of the plug 144 as it passes into the enlarged portion. Projections 142h extending radially inward from the axial ribs limit the axial movement of the plug and prevent it from falling into the liquid container.

In the foregoing embodiments, the holder is provided with the screw cap at its end. However, the screw cap and the inner sleeve may be integrally formed with the vial internally inserted. The holder described above covers an overall body of the medicine bottle; however, any holding member may be used as long as the medicine bottle is axially movable.

While two embodiments of an infusion unit have been described and illustrated herein, many other constructions will be apparent to those skilled in the art. Additionally, a large number of materials of construction may be used including a variety of plastics to construct the holder and coupling portion and a variety of elastomers in place of the above-mentioned rubber for the plug and ring. It is therefore to be understood that, within the scope of the appended claims, the invention may be practiced otherwise than specifically described.

We claim:

1. An infusion unit, adapted for use with a vial having a pierceable mouth stopper, comprising:
- a flexible container;
- an open-ended pipe having an axis, a first opening of the pipe in communication with the container, a second opening axially opposite the first opening and at least two portions of different internal diameters, a larger diameter portion, and a smaller diameter portion, said smaller diameter portion being located between the second opening and the larger diameter portion;
- an axially moveable plug disposed in said smaller diameter portion for sealing the second opening of the pipe; and
- an engaging member having one end for engaging the plug and another end having a needle for piercing the mouth stopper of the vial, said engaging member being axially moveable within the pipe.

2. The infusion unit of claim 1, further comprising an annular flange at one end of the engaging member unitarily formed with said needle extending therefrom.

3. The infusion unit of claim 2, wherein said engaging member includes an annular top surrounding the needle and a collar extending from the annular top to surround the pipe.

4. The infusion unit of claim 3, wherein said annular top and collar are unitarily formed with said needle, the annular top being directly connected to the needle.

5. The infusion unit of claim 2, wherein said engaging member further comprises an inner collar surrounded by said pipe and extending from the end of the engaging member to the annular top.

6. The infusion unit of claim 1, further comprising a first sleeve coaxial with and surrounding said pipe and engaging member, said first sleeve secured at a first end to the pipe adjacent the first opening of the pipe.

7. The infusion unit of claim 6, further comprising a second sleeve coaxial with and surrounded by said first sleeve and axially moveable relative thereto, said second sleeve for receiving the vial in an orientation having the mouth stopper facing the needle.

8. The infusion unit of claim 7, further comprising an end cap for closing the upper end of said second sleeve.

9. The infusion unit of claim 7, further comprising an elastomeric ring at a lower end of the second sleeve and in slidable contact with the first sleeve for forming a seal with said vial.

10. The infusion unit of claim 8, further comprising a hanger secured to the end cap, said hanger flexible between a first position for preventing axial movement of the second sleeve and a second position for permitting axial movement of the second sleeve.

11. An infusion unit comprising:
- a holding member for holding a medicine bottle, said bottle having a mouth sealed by a pierceable mouth-plug and movable along an axial direction;
- a flexible liquid container;
- communicating means for communication between the interior of said medicine bottle and the interior of said flexible liquid container;
- said communicating means comprising
- a communicating pipe having two openings and an enlarged inner diameter portion formed at a region axially intermediate said openings;
- a frictional plug member for sealing a first of said two openings of said communicating pipe located adjacent the medicine bottle; and
- a movable cap positioned partially within said communicating pipe and having a piercing needle axially projecting from a top of said movable cap toward said pierceable mouth-plug of said medicine bottle, said needle having a lower end disposed within the communicating pipe;
- said movable cap member being movable between:
- (1) a first position where said frictional plug member is located between said enlarged diameter portion of said communicating pipe and said first opening and in contact with the lower end of said piercing needle so that said movable cap member is prevented from moving toward said flexible liquid container, said piercing needle being adapted to pierce through said pierceable mouth-plug of said medicine bottle as said medicine bottle is moved toward said flexible liquid container; and
- (2) a second position where, when the pierceable mouth-plug of the medicine bottle is brought into contact with the top of the movable cap and is further moved toward the flexible liquid container, said frictional plug member adapted to be forced by said lower end of said piercing needle into said enlarged diameter portion of said communicating pipe to create a passageway between the frictional plug and the pipe.

* * * * *